(12) United States Patent
Hansen et al.

(10) Patent No.: US 7,967,220 B2
(45) Date of Patent: Jun. 28, 2011

(54) MANUAL SPRAYER WITH DUAL BAG-ON-VALVE ASSEMBLY

(75) Inventors: Eric J. Hansen, Ada, MI (US); Kevin Haley, Byron Center, MI (US); Jesse J. Williams, Zeeland, MI (US); Herbert J. VanderBilt, Lowell, MI (US); Michael R. Foote, Ada, MI (US); Donald J. Mahaffy, Zeeland, MI (US)

(73) Assignee: BISSELL Homecare, Inc., Grand Rapids, MI (US)

( * ) Notice: Subject to any disclaimer, the term of this patent is extended or adjusted under 35 U.S.C. 154(b) by 126 days.

(21) Appl. No.: 12/345,892

(22) Filed: Dec. 30, 2008

(65) Prior Publication Data

US 2009/0108021 A1    Apr. 30, 2009

Related U.S. Application Data

(63) Continuation-in-part of application No. 10/604,780, filed on Aug. 15, 2003, now Pat. No. 7,906,473.

(60) Provisional application No. 60/319,548, filed on Sep. 13, 2002, provisional application No. 61/036,706, filed on Mar. 14, 2008.

(51) Int. Cl.
*A62C 13/62* (2006.01)
(52) U.S. Cl. ......................................... 239/304; 239/373
(58) Field of Classification Search .......... 239/302–308, 239/310–312, 337, 390, 391, 373; 222/94, 222/145.3, 144.5
See application file for complete search history.

(56) References Cited

U.S. PATENT DOCUMENTS

| | | | |
|---|---|---|---|
| 3,241,722 A | 3/1966 | Nissen | |
| 3,325,056 A | 6/1967 | Lewis | |
| 3,416,709 A | 12/1968 | Shultz et al. | |
| 3,488,287 A | 1/1970 | Seglin et al. | |
| 3,521,792 A | 7/1970 | Davidson | |
| 3,638,786 A | 2/1972 | Borecki et al. | |
| 3,722,752 A | 3/1973 | Kenkare et al. | |
| 3,722,753 A | 3/1973 | Miles | |
| 3,731,847 A | 5/1973 | Webster | |
| 3,819,524 A | 6/1974 | Schubert et al. | |
| 3,866,800 A | 2/1975 | Schmitt | |
| 3,961,756 A | 6/1976 | Martini | |
| 3,970,219 A | 7/1976 | Spitzer et al. | |

(Continued)

FOREIGN PATENT DOCUMENTS

EP    0313414 A1    4/1989

(Continued)

*Primary Examiner* — Davis Hwu
(74) *Attorney, Agent, or Firm* — McGarry Bair PC

(57) ABSTRACT

A manual spray dispenser for dispensing a mixture of two compositions comprises a container having a first and second chamber and a single dispensing spray outlet for dispensing controlled amounts of liquids from each of the first and second chambers. At least one of the chambers has a separator in the form of a pouch for physically separating the contents of the container from an interior surface of the chamber. The first chamber can contain a first composition and the second chamber can contain a second composition having a reactive component that reacts with at least one compound upon contact or mixing. The dispenser further contains a dispensing system for simultaneously dispensing the first composition and the second composition from their respective first and second chambers, mixing the two compositions together, and dispensing a mixture of the two compositions from the container under pressure.

26 Claims, 7 Drawing Sheets

U.S. PATENT DOCUMENTS

| | | |
|---|---|---|
| 3,970,584 A | 7/1976 | Hart et al. |
| 4,019,657 A | 4/1977 | Spitzer et al. |
| 4,534,511 A * | 8/1985 | Sullivan .................. 239/336 |
| 4,585,149 A * | 4/1986 | Zulauf .......................... 222/94 |
| 4,839,081 A | 6/1989 | Church et al. |
| 4,893,593 A | 1/1990 | Sejimo et al. |
| 5,215,675 A | 6/1993 | Wilkins et al. |
| 5,421,492 A | 6/1995 | Barger et al. |
| 5,702,033 A * | 12/1997 | Beaver ......................... 222/94 |
| 5,767,055 A | 6/1998 | Choy et al. |
| 5,925,608 A | 7/1999 | Spruyt et al. |
| 6,021,926 A | 2/2000 | Lauwers et al. |
| 6,347,726 B1 * | 2/2002 | Jackson et al. .................. 222/94 |
| 6,651,847 B2 | 11/2003 | Mekata et al. |
| 6,824,623 B1 | 11/2004 | Gross et al. |
| 6,880,515 B2 | 4/2005 | Geyer et al. |
| 2004/0226964 A1 | 11/2004 | Bourque et al. |

FOREIGN PATENT DOCUMENTS

| | | |
|---|---|---|
| WO | 9621605 A1 | 7/1996 |
| WO | 9919075 A1 | 4/1999 |

* cited by examiner

MANUAL SPRAYER WITH DUAL BAG-ON-VALVE ASSEMBLY

CROSS REFERENCE TO RELATED APPLICATIONS

This application is a continuation in part of U.S. application Ser. No. 10/604,780, filed Aug. 15, 2003, now U.S. Pat. No. 7,906,473, issued Mar. 15, 2011, which claims the benefit of U.S. Provisional Application Ser. No. 60/319, 548, filed Sep. 13, 2002, and this application further claims the benefit of U.S. Provisional Application Ser. No. 61/036,706, filed Mar. 14, 2008, entitled "Manual Spray Cleaner", both of which are incorporated by reference.

BACKGROUND OF THE INVENTION

1. Field of the Invention

This invention relates to dispensers for dispensing one or more compounds under pressure. In one of its aspects, the invention relates to a dispenser for spraying a cleaning composition on a surface to be cleaned. In yet another aspect, the invention relates to a dispenser for dispensing a mixture to neutralize a chemical or biological species. In still another aspect, the invention relates to a dispenser for dispensing a mixture of at least two components that react to perform a desired chemical reaction.

2. Description of the Related Art

Many types of compositions in fields ranging from cleaning to health and beauty aids, paints, arts and crafts and neutralization of chemical and biological agents comprise one or more components that have optimal performance when mixed or activated just prior to or at the point of use. For example, the performance of cleaning compositions with an oxidizing agent deteriorates over a relatively short time if the cleaning composition and oxidizing agent are stored together in a single chamber. In another example, most at-home hair-dying kits require the colorant to be stored separately from the activator.

Various systems have been developed to separately store two-component compositions and mix the components during or immediately prior to use. For example, in the field of cleaning, the Choy et al. U.S. Pat. No. 5,767,055 discloses an apparatus for cleaning a hard surface, such as kitchen and bathroom tile, comprising a dual chamber bottle having a spray applicator for dispensing a mixture of compositions from each of the two chambers. One of the chambers contains a builder or chelating agent composition and the other chamber includes a hypohalite or hypohalite generator such as sodium hypochlorite as a bleaching agent. The two components of the composition are mixed upon spraying onto a surface.

The Kobyashi et al. U.S. Pat. No. 5,869,440 and the Unilever PCT Publication No. WO 95/16023 both disclose two part bleaching compositions which comprise a peroxide composition and a detergent composition which are stored separately and sprayed onto hard surfaces at the time of combination.

The Van Dyck et al. U.S. Pat. No. 3,635,372 discloses a housing mounting a pair of aerosol chambers, one containing an incapacitating fluid and the other containing a gas. The aerosol chambers have output valves that are connected through tubes to an output nozzle and a whistle. A trigger is pivotally mounted to the housing and moves laterally to displace a vertically movable actuator for simultaneously opening both aerosol valves in the chambers for dispensing the fluid and gas in the chambers.

The Breslau et al. U.S. Pat. No. 3,303,970 and the Safianoff U.S. Pat. No. 3,575,319 disclose a pair of aerosol dispensing chambers having different fluids that are dispensed through outlet valves connected through tubing to a single dispensing orifice. The outlet valves are actuated simultaneously by a trigger that is pivotally mounted to a frame that holds the aerosol chambers. Rotation of the trigger forces the valves downwardly to open the valves simultaneously.

Another field that utilizes compositions that have one or more components that should not be mixed or activated until just prior to or at the point of use is the field of chemical and biological neutralization and decontamination. For example, U.S. Pat. No. 6,566,574 to Tadros et al., U.S. Pat. No. 7,390, 432 to Tucker, and U.S. Pat. Nos. 7,271,137, 6,723,890 and 7,125,497 to Tucker et al., herein incorporated in full by reference, disclose multi-component formulations for neutralizing several types of chemical and biological species. The formulations include at least one reactive component, comprising an oxidizing agent, a nucleophilic agent, a reducing agent, an acid or combinations thereof that reacts with the chemical or biological species to neutralize it and render it effectively harmless to human and animal life. The formulations can be provided in kits that store the reactive component separately from the rest of the formulation until just prior to use. Storing the reactive component separately can increase the stability, shelf-life and effectiveness of the formulation.

The basic components of these neutralizing and decontamination formulations include one or more solubilizing agents and one or more reactive compounds. Additionally, the formulations can include a peroxide activator or a bleaching activator. The solubilizing agent can be a cationic surfactant, a cationic hydrotrope, a fatty alcohol or mixtures thereof. For example, U.S. Pat. Nos. 6,566,574 and 6,723,890 disclose formulations that comprise one or more solubilizing agents to solubilize the chemical or biological species for reaction with the reactive compound. The reactive compound can be selected from the group comprising hydrogen peroxide, urea hydrogen peroxide, an activated peroxide compound (such as hydrogen peroxide and a bicarbonate salt), hydroperoxycarbonate, oximates, alkoxides, aryloxides, aldehydes, peroxymonosulfate, Fenton's reagent and sodium hypochlorite.

The neutralizing and decontamination formulation can also contain one or more peroxide activators selected from the group consisting of potassium bicarbonate, sodium bicarbonate, ammonium bicarbonate, ammonium hydrogen bicarbonate, lithium bicarbonate, ammonium carbonate, and potassium carbonate.

U.S. Pat. Nos. 7,271,137 and 7,390,432 disclose a neutralizing and decontamination formulation similar to those disclosed in U.S. Pat. Nos. 6,566,574 and 6,723,890 called DF-200. DF-200 comprises one or more solubilizing agents, one or more reactive compounds and a bleaching activator. The bleaching activator improves the reaction kinetics of the reactive compound and can eliminate the need to adjust the pH of the formulation. Suitable bleaching activators include compounds selected from the group consisting of ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, propylene glycol diacetate, tetraacetyl ethylenediamine (TAED), and n-nonanoyloxy-benzenesulfonate (NOBS).

U.S. Pat. No. 7,125,497 discloses a formulation for neutralizing toxic industrial chemicals comprising a cationic surfactant and hydrotrope as a solubilizing agent and one or more reactive compounds. The reactive compounds can be an acid, such as sodium sulfate and acetic acid, or a reducing compound, such as sodium bisulfite or sodium borohydride, for example.

The neutralizing and decontamination formulations can be provided in two-part kits wherein the reactive component is stored separately from the solubilizing agents and activators. The two parts of the kit can be mixed just prior to use.

SUMMARY OF THE INVENTION

According to the invention, a kit for dispensing a mixture of two compositions comprises a container comprising a first chamber and a second chamber, wherein at least one of the first and second chambers has a separator in the form of a pouch for physically separating contents of the chamber from an interior surface of the chamber and a dispensing system, The dispensing system is connected to the first and second chambers and has a single dispensing spray outlet for simultaneously dispensing and mixing controlled amounts of liquid from each of the first and second chambers. The kit also comprises a first composition comprising a solubilizing composition and a second composition different from the first composition and having a reactive component that reacts with at least one compound upon mixing. An aerosol propellant is provided between the separator and the interior surface of the at least one of the first and second chambers for pressurizing the contents in the pouch for dispensing the contents thereof through the dispensing system under pressure. When the first composition is stored in the first chamber and the second composition is stored in the second chamber, the dispensing system can simultaneously dispense a mixture of the first and second compositions from the container under pressure.

According to one embodiment of the invention, the first composition is a cleaning composition and the second composition is an oxidizing composition. The cleaning composition can comprise at least one of solvent, a surfactant, an anti-stain compound, an anti-soil compound, a fragrance and mixtures thereof. The oxidizing composition can comprise at least one of an oxidizing agent, an anti-stain compound, an anti-soil compound, a stabilizer and mixtures thereof. The oxidizing agent can be selected from the group consisting of hydrogen peroxide, percarboxylic acids and salts, percarbonic acids and salts, perimidic acids and salts, peroxymonosulfuric acids and salts, and mixtures thereof.

According to another embodiment of the invention, the solubilizing composition can comprise at least one of a cationic surfactant, a cationic hydrotrope, a fatty alcohol and mixtures thereof. The cationic surfactant can comprise at least one of a quaternary ammonium salt, a polymeric quaternary salt and mixtures thereof. The cationic hydrotrope can comprise at least one of tetrapentyl ammonium bromide, triacetyl methyl ammonium bromide, tetrabutyl ammonium bromide and mixtures thereof. The fatty alcohol can comprise an alcohol having 8-20 carbon atoms. The solubilizing composition can also comprise at least one bleaching activator selected from the group consisting of ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, propylene glycol diacetate, tetraacetyl ethylenediamine (TAED), and n-nonanoyloxybenzenesulfonate (NOBS). The solubilizing composition can also comprise at least one peroxide activator selected from the group consisting of potassium bicarbonate, sodium bicarbonate, ammonium bicarbonate, ammonium hydrogen bicarbonate, lithium bicarbonate, ammonium carbonate, and potassium carbonate.

According to yet another embodiment of the invention, the reactive component comprises at least one of an oxidizing agent, a reducing agent, a nucleophilic agent, an acid and mixtures thereof. The oxidizing agent is selected from the group consisting of hydrogen peroxide, urea hydrogen peroxide, hydroperoxycarboflate, peracetic acid, sodium perborate, sodium peroxypyrophosphate, sodium peroxysilicate, sodium percarbonate, hydroperoxycarbonate, peroxymonosulfate, Fenton's reagent and sodium hypochlorite. The nucleophilic agent is selected from the group consisting of oximates, alkoxides, aryloxides and aldehydes. The reducing agent is selected from the group consisting of sodium bisulfite, ferrous sulfide, sodium sulfide, sodium thioglycollate, sodium thiosulfate and sodium borohydride. The acid is selected from the group consisting of sodium bisulfate, citric acid, acetic acid, nitrous acid, hydrocyanic acid, hydrogen sulfide and phenols.

According to another embodiment of the invention, a method for neutralizing at least one of a chemical or biological species includes filling a first pouch in a first chamber with a solubilizing composition comprising at least one solubilizing agent for solubilizing the at least one of a chemical and biological species and filling a second pouch in a second chamber with a reactive composition comprising at least one reactive component that acts on the at least one of a chemical and biological species solubilized by the at least one solubilizing agent and simultaneously spraying the solubilizing composition and the reactive composition under pressure from their respective first and second pouches onto the at least one chemical or biological species. The method further includes injecting an aerosol propellant in a space between the first pouch and the first chamber and the second pouch and the second chamber to pressurize the first and second pouches, respectively, prior to the spraying act.

In one embodiment, the method can further include mixing the solubilizing and reactive compositions together as they are sprayed onto the chemical or biological species. Alternatively, the solubilizing and reactive compositions can be mixed together just prior to being sprayed onto the chemical of biological species.

In another embodiment, the solubilizing and reactive compositions can be sprayed in equal amounts from their respective first and second chambers. Alternatively, the solubilizing and reactive compositions can be dispensed in unequal amounts. The solubilizing and reactive compositions can be selectively dispensed under pressure as a mist, a spray, a stream or combinations thereof.

In yet another embodiment, the solubilizing composition comprises at least one of a cationic surfactant, a cationic hydrotrope, a fatty alcohol and mixtures thereof. The reactive component comprises at least one of an oxidizing agent, a reducing agent, a nucleophilic agent, an acid and mixtures thereof.

According to another embodiment, the solubilizing composition further comprises at least one bleaching activator selected from the group consisting of ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, propylene glycol diacetate, tetraacetyl ethylenediamine (TAED), and n-nonanoyloxybenzenesulfonate (NOBS). In another embodiment, the solubilizing composition further comprises a peroxide activator selected from the group consisting of potassium bicarbonate, sodium bicarbonate, ammonium bicarbonate, ammonium hydrogen bicarbonate, lithium bicarbonate, ammonium carbonate, and potassium carbonate.

BRIEF DESCRIPTION OF THE DRAWINGS

The invention will now be described with reference to the accompanying drawings in which.

DESCRIPTION OF THE PREFERRED EMBODIMENT

Figure 1:
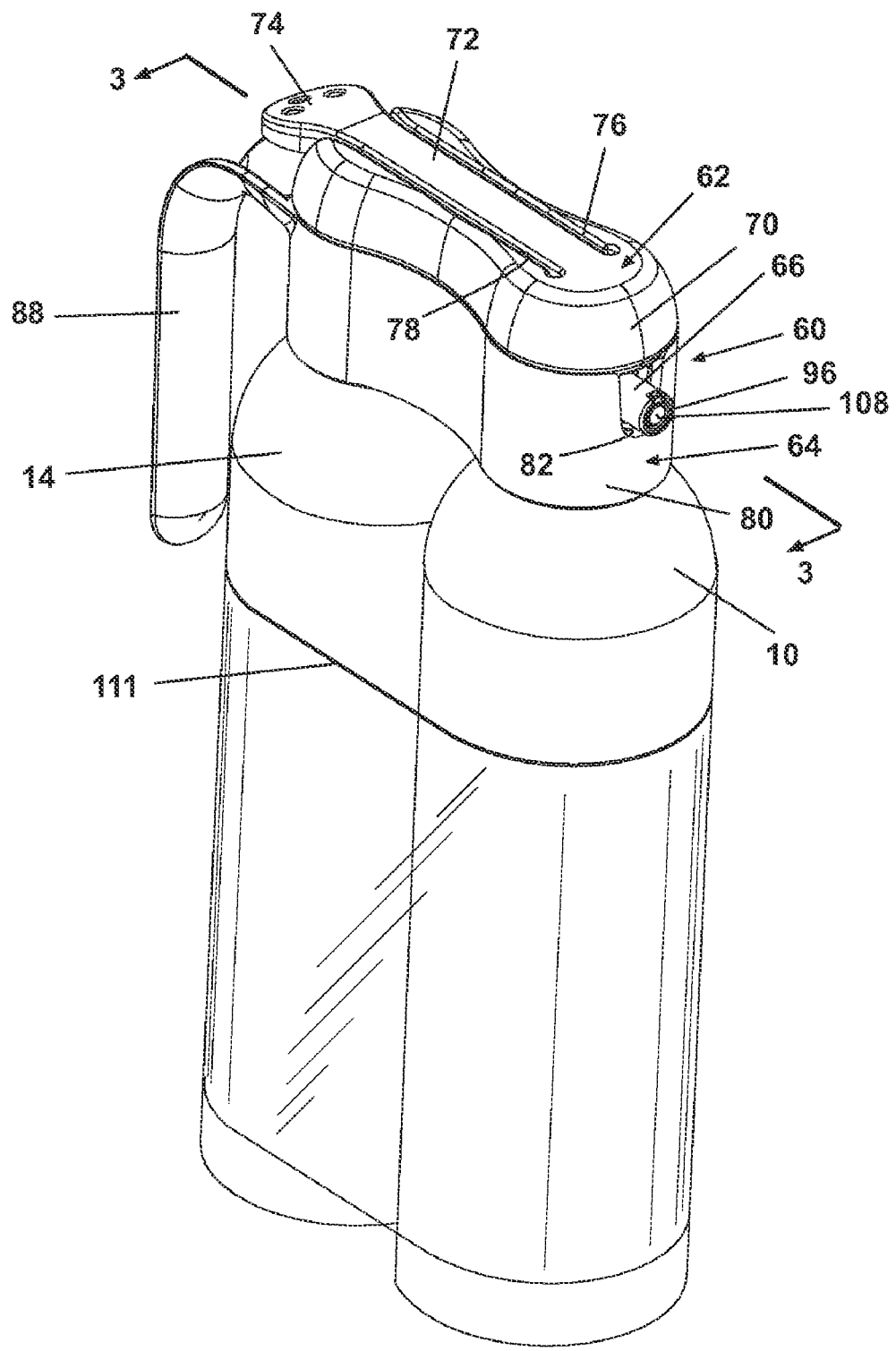
FIG. 1 is a perspective view of an aerosol dispenser according to one embodiment of the invention.

Referring now to the drawings, FIGS. 1 through 3A, there is shown an embodiment of an aerosol dispenser 60 comprising a push valve assembly 110 for each chamber 10, 14, an actuator top 62, a handle base 64, and a dispensing tube 66. Aerosol chambers 10 and 14 are releasably mounted within the handle base 64.

Figure 3:
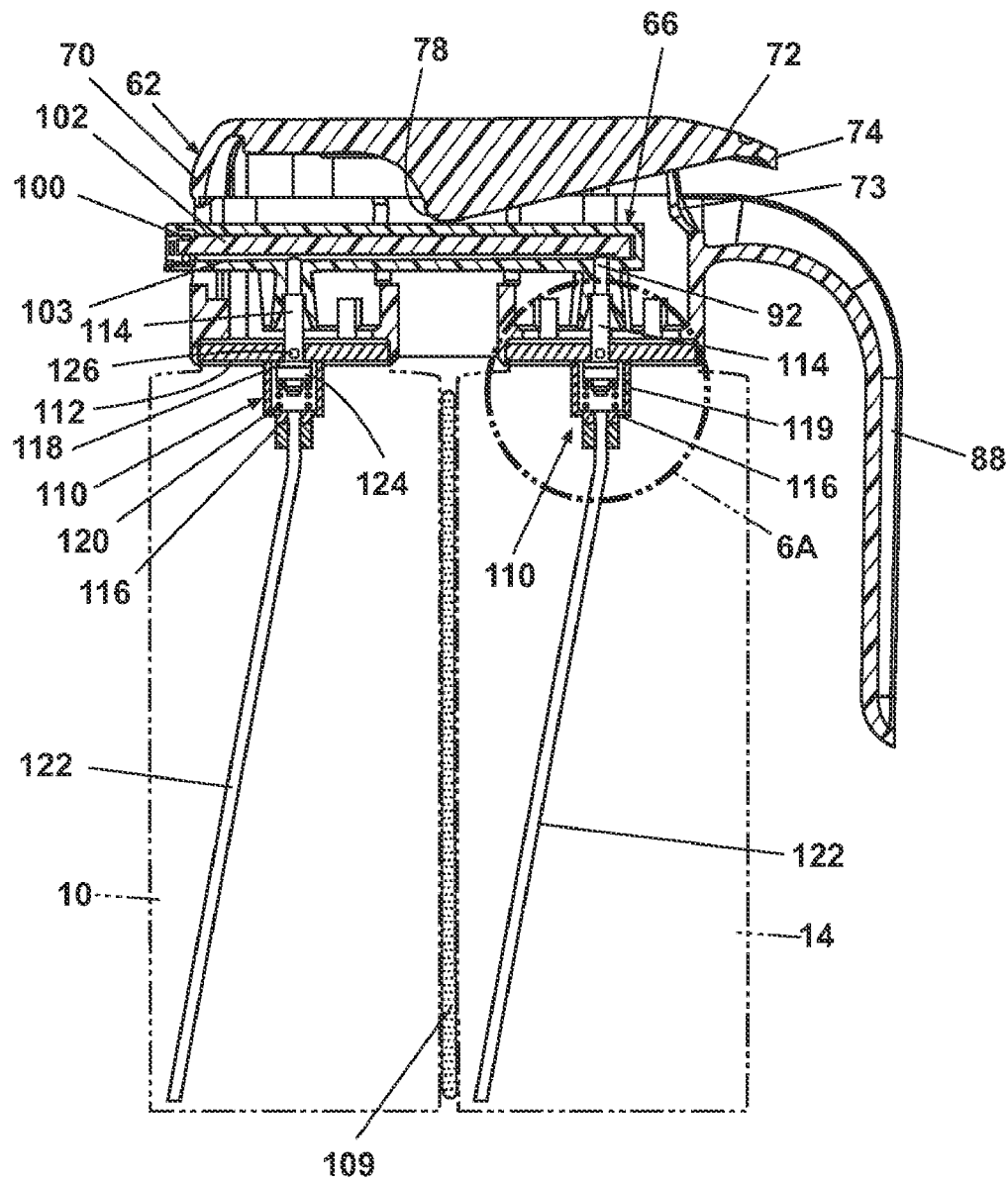
FIG. 3 is a sectional view of the aerosol dispenser illustrated in FIG. 1 taken along line 3-3 of FIG. 1.
Figure 3A:
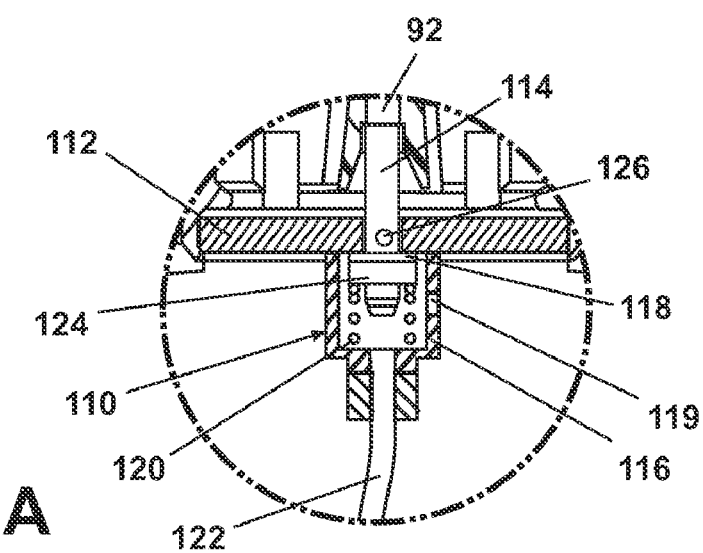

As depicted in FIG. 3, the push valve assembly 110 comprises a valve cup 112, a stem 114, a housing 116, a gasket 118, a spring 120, and a dip tube 122. The valve cup 112 has an annular lip sized to receive chamber 10 or 14. Further, the center of the valve cup 112 has an opening 126 therethrough. Preferably, the valve cup 112 is formed of the same material as the chambers 10, 14 and lined with a suitable separator material as described above for the chambers. Specifically, the chamber 10, 14 and valve cup 112 are made of the same material type and preferably are comprised of aluminum. Alternatively, these components can be made of steel or tin-plated steel. Valve cup 112 may optionally comprise a separator, or liner, as described above. The valve stem 114 has a solid lower end, a hollow upper end, a reduced diameter section therebetween, and preferably one, and optionally two, valve orifices located in the side that are in fluid communication with the hollow upper end. The valve stem 114 is received in the opening 126 of the valve cup 112, with the gasket 118 located between the solid lower end of the stem 114 and the cup 112. The housing 116 has a hollow cylindrical upper portion, a reduced diameter hollow lower portion, and a flange therebetween. The housing 116 surrounds the stem 114, abuts the gasket 118 at its upper end, and is secured in place by the valve cup 112. Inside the housing 116, the spring 120 is positioned between the lower end of the stem 114 and the flange of the housing 116 and biases the stem 114 such that the valve orifices are positioned at or above the gasket 118. The hollow dip tube 122 is connected to and in fluid communication with the lower portion of the housing 116 and extends to the bottom of the chamber 10 or 14.

The stem 114 and the housing 116 are made from nylon or polypropylene depending upon the propellant used and the nature of the composition. In the cleaner composition, any propellant may be used and nylon is the preferred material for the stem 114 and housing 116. In the peroxygen container, nylon is preferred when HFC is the aerosol propellant. Polypropylene may be used when any propellant other than HFC is utilized. The gasket 118 is preferably formed from a resilient material, such as Buna-Nitrile (Buna-N) or Butyl, common gasket materials used in the aerosol dispenser industry. The spring 120 and the dip tube 122 are preferably composed of stainless steel and polyethylene, respectively. The invention should not be limited to the type of push valve assembly 110 described herein, and other push valves well known to those skilled in the art can be utilized with the aerosol dispenser.

The actuator top 62 has a cover housing 70 with an integrally formed actuator finger 72 and a thumb tab 74. The actuator finger 72 is separated along its sides by slots 76, has cam levers 78 that extend downward therefrom, and is resiliently cantilevered from a front portion of the cover housing 70. The actuator top 62 is formed from a resilient plastic material, preferably by injection molding. Alternatively, it is contemplated that the actuator finger 72 can be connected to the cover housing 70 via a hinged arrangement (not shown) instead of an integral connection.

Figure 2:
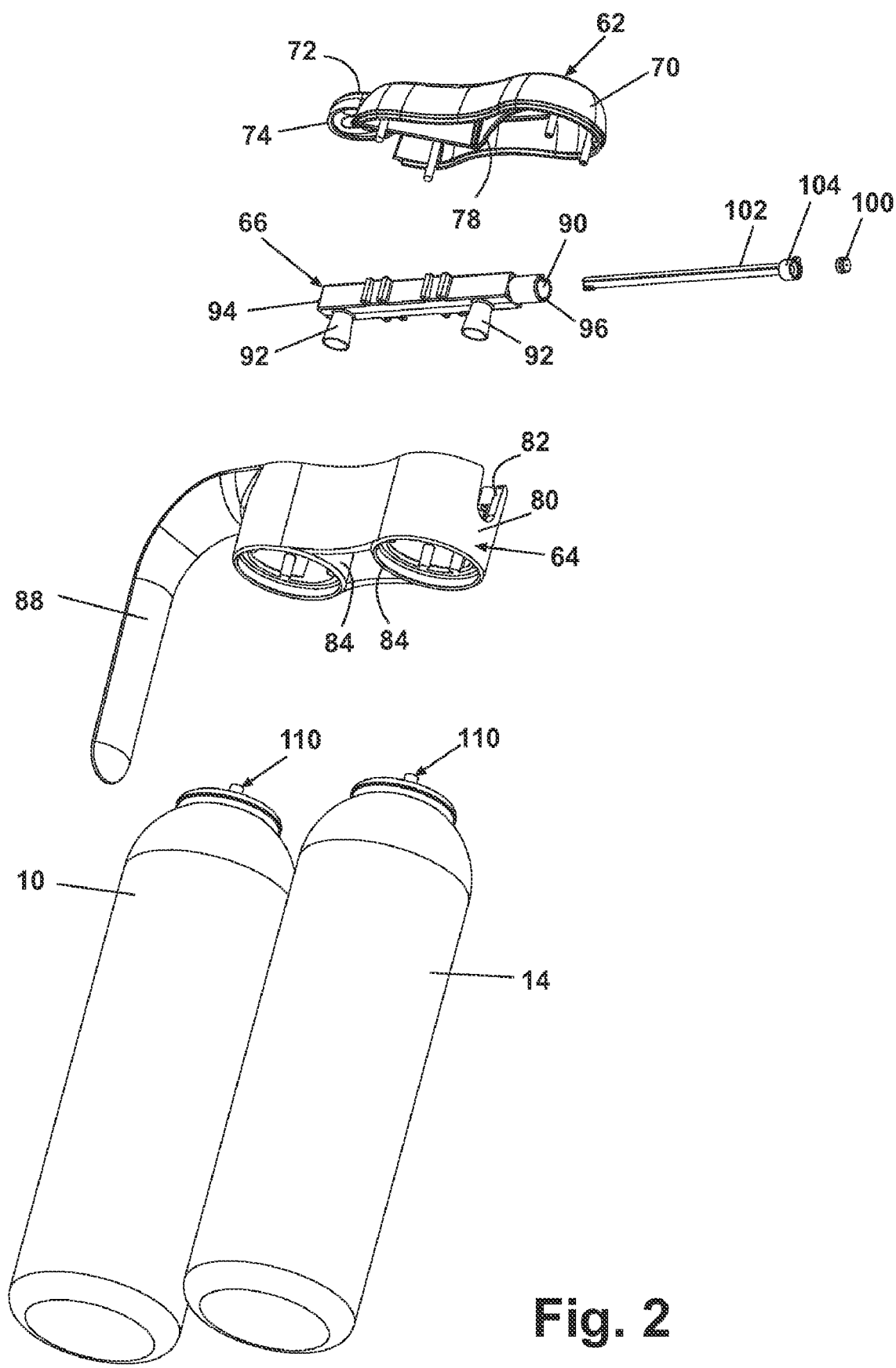
FIG. 2 is an exploded view of the aerosol dispenser illustrated in FIG. 1.

The handle base 64, best shown in FIG. 2, comprises an outer wall 80 having a slot 82 at one end in which is mounted the end of the dispensing tube 66. The handle base 64 further comprises a pair of arcuate inner walls 84, which with outer wall 80 forms cylindrical sockets for the aerosol chambers 10 and 14. The arcuate inner walls 84 each have a vertical slot extending from a top portion substantially identical with the slot 82 in the outer wall 80. A handle 88 is integrally formed with the outer wall 80 and is designed so that a user can grip the handle 88 with his or her hand and apply thumb pressure at thumb tab 74 to the actuator finger 72. An integral lock (not shown) can be formed on an outer end of the actuator finger 72 and project downwardly thereof to abut the handle 88 and prevent depression of the actuator finger 72 prior to sale and use of the dispenser. The integral lock can be attached to the handle 88 with a frangible connection and thus easily removed when it is desirable to dispense the contents of the aerosol chambers 10 and 14.

Figure 4:
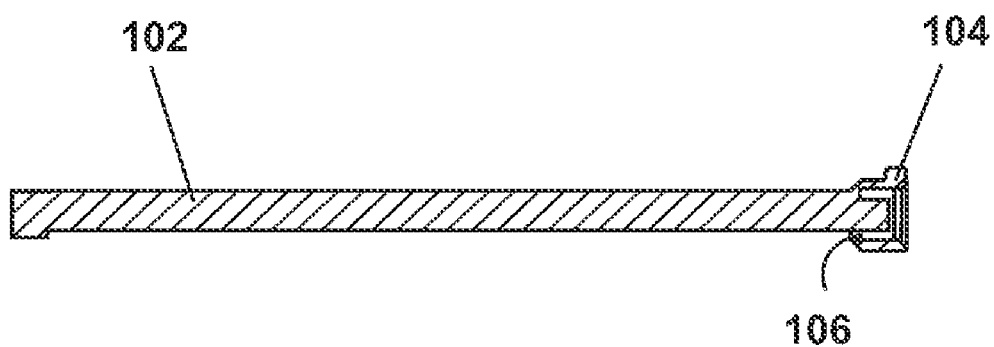
FIG. 4 is a sectional view of a hollow conduit insert illustrated in FIG. 2.
Figures 5, 6:
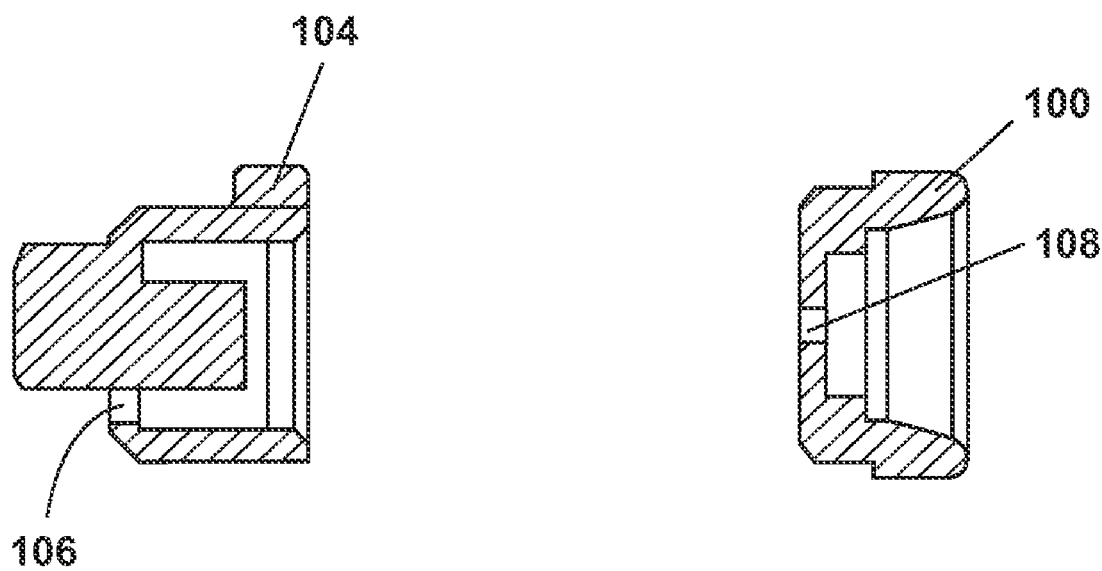
FIG. 5 is a sectional view of a mechanical breakup plug of the hollow conduit insert illustrated in FIG. 2.
FIG. 6 is a sectional view of a terminal orifice of the hollow conduit insert illustrated in FIG. 2.

Referring to FIGS. 2-6, the dispensing tube 66, preferably formed from polypropylene, comprises connecting tubes 92 in fluid communication with the interior of a hollow conduit 90 having a closed end 94 and a nozzle end 96. The connecting tubes 92 have an open lower end sized to receive the hollow upper end of the valve stem 114. Dispensing tube 66 further comprises a hollow conduit insert 102. Hollow conduit insert 102 is a rod shaped structure that fits tightly against an upper wall of the hollow conduit 90 but leaves a cavity 103 of a predetermined volume at a lower wall of the hollow conduit 90. The cavity is in fluid communication with connecting tubes 92 and, therefore, with the hollow upper end of the valve stem 114. A mechanical breakup plug 104, best seen in FIGS. 4 and 5, is located on one end of the conduit insert 102 and forms a part of the nozzle end 96. A spray aperture 106 of a predetermined size is formed at a lower portion of the mechanical breakup plug 104 and aligned with the cavity 103.

A terminal orifice 100, best seen in FIG. 6, is fixedly attached to the mechanical breakup plug 104 and comprises an at least one generally circular terminal aperture 108, preferably having a diameter in the range of 0.020 to 0.040 inches, therethrough that is in fluid communication with the spray aperture 106 and, therefore, the cavity 103 and the connecting tubes 92. The mechanical breakup plug and the terminal orifice force a disrupted flow pattern at the nozzle end 96 of the hollow conduit 90 wherein the contents are mixed and delivered under pressure to the surface to be cleaned.

The sealed and pressurized chamber is capable of containing excessive pressure created if the oxidant should come in contact with a reactant inside the chamber, such as flaws in the separator material, contact with an activator, or trace contaminants in the compounding solvents. The chamber is designed to an aerosol industry standard 18 bar strength level to provide an adequate safety margin. In the preferred embodiment, the chamber buckle strength is no less than 250 psi and the burst strength no less than 320 psi.

Figure 7:
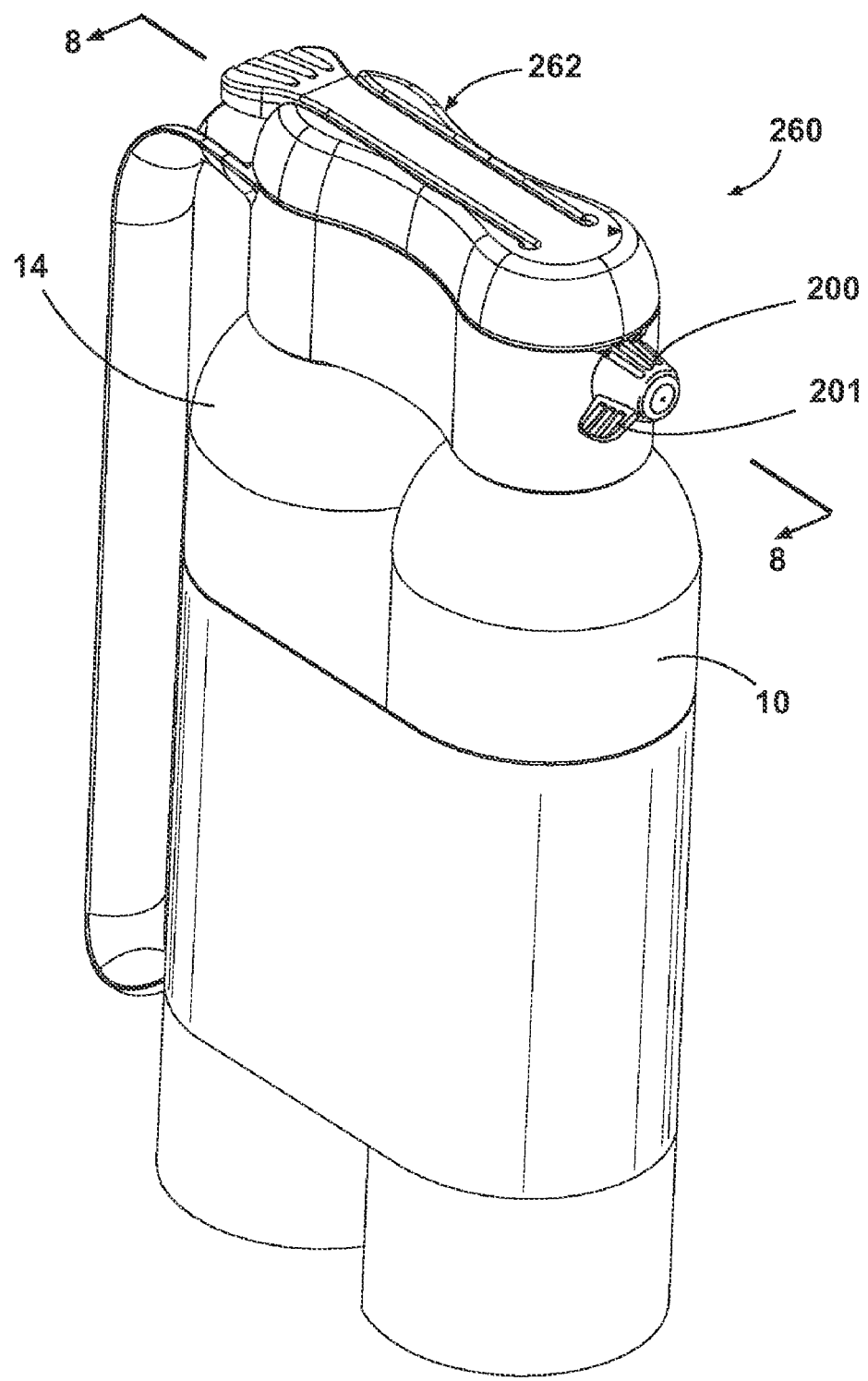
FIG. 7 is a perspective view of a second embodiment of an aerosol dispenser according to the invention.

FIG. 7 illustrates a manual spray dispenser 260 similar to the spray dispenser 60, except that each chamber 10, 14 can have a separator 250 in the form of a bag or a pouch according to another embodiment of the invention. Therefore, elements in the dispenser 260 similar to those of dispenser 60 will be numbered with the prefix 200.

Figure 8:
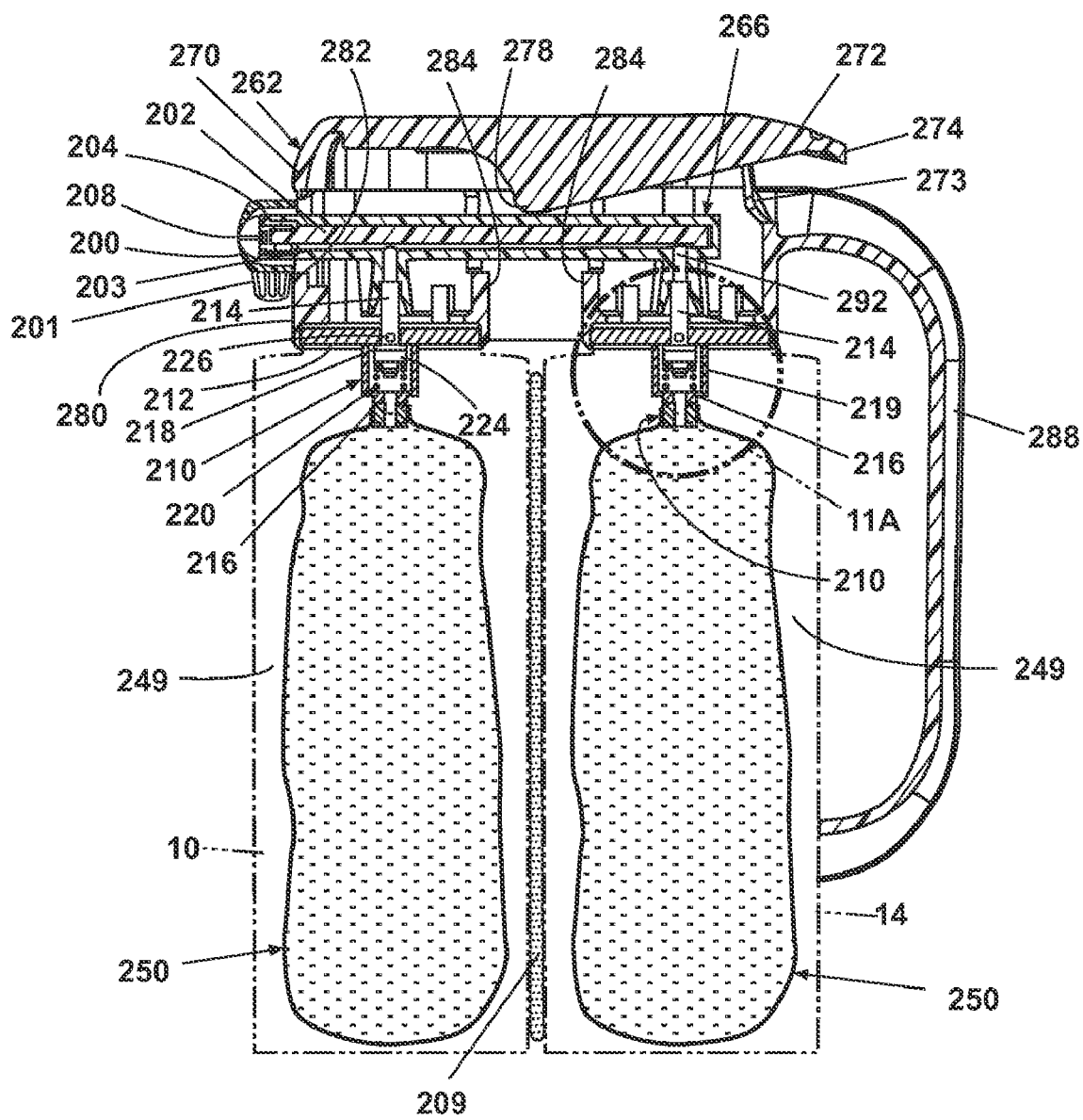
FIG. 8 is a sectional view of the aerosol dispenser illustrated in FIG. 7 taken along line 8-8 of FIG. 7.

As illustrated in FIG. 8, a quantity of compressed propellant gas 249 is contained within the chamber 10, 14, surrounding the separator 250 to provide the propellant force necessary to dispense the contents of the composition stored within the separator 250.

The aerosol dispenser 260 can have a push valve assembly 210 for each chamber 10, 14, an actuator top 262, a handle base 264, and a dispensing tube 266. Aerosol chambers 10 and 14 are releasably mounted within the handle base 264.

Figure 8A:
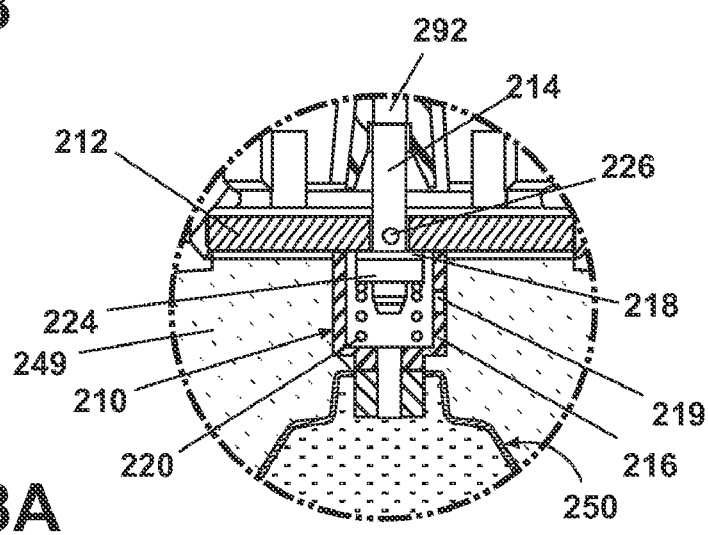
FIG. 8A is an enlarged view of a portion of the aerosol dispenser illustrated in FIG. 8.

As depicted in FIGS. 8 and 8A, the push valve assembly 210 comprises a valve cup 212, a stem 214, a housing 216, a gasket 218 and a spring 220. The valve cup 212 has an annular lip sized to receive chamber 10 or 14. Further, the center of the valve cup 212 has an opening 226 therethrough. The chambers 10, 14 and valve cup 212 can be made of the same material type and preferably are comprised of aluminum. Alternatively, these components can be made of steel or tin-plated steel.

The valve stem 214 has a solid lower end, a hollow upper end, a reduced diameter section therebetween, and preferably one, and optionally two, valve orifices located in the side that are in fluid communication with the hollow upper end. The valve stem 214 is received in the opening 226 of the valve cup 212, with the gasket 218 located between the solid lower end of the stem 214 and the cup 212.

The housing 216 has a hollow cylindrical upper portion, a reduced diameter hollow lower portion, and a flange therebetween. The housing 216 surrounds the stem 214, abuts the gasket 218 at its upper end, and is secured in place by the valve cup 212. Inside the housing 216, the spring 220 is positioned between the lower end of the stem 214 and the flange of the housing 216 and biases the stem 214 such that the valve orifices are positioned at or above the gasket 218. The lower end of the housing 216 can be provided with a fluid flow channel 222 for fluidly connecting the push valve assembly 210 with the contents of the chambers 10, 14.

The invention in its broader embodiments is not limited to the type of push valve assembly 210 described herein. Other push valves well known to those skilled in the art can be utilized with the aerosol dispenser according to the invention. Another example of a push valve assembly can be found in U.S. Publication No. 20090236363, filed Mar. 13, 2009, entitled "Manual Spray Cleaner".

Figure 9:
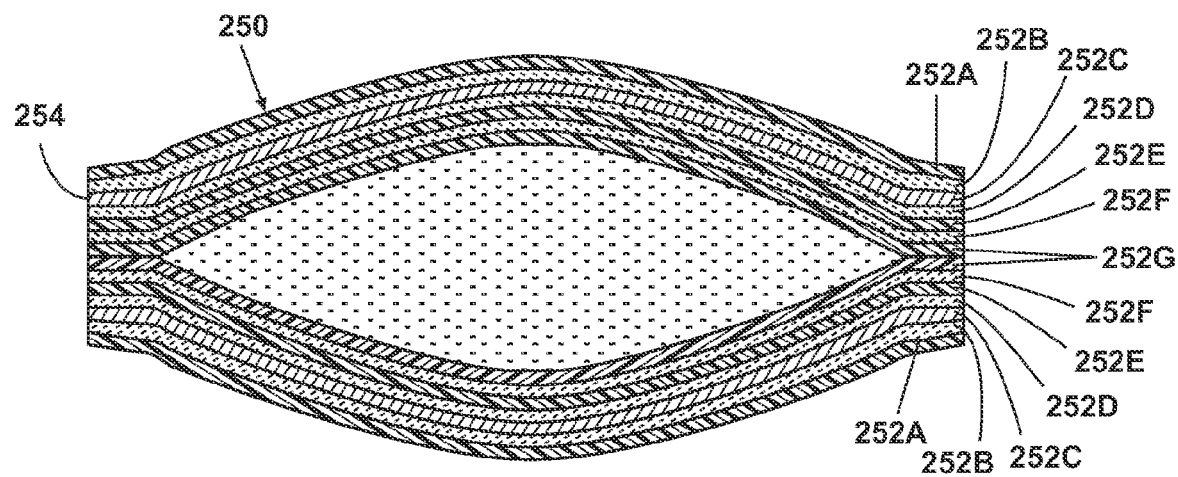
FIG. 9 is a cross sectional view of a laminated separator bag according to the invention.

The separator 250 can be a polyethylene or polypropylene bag or can comprise multiple layers 252 of one or more flexible materials laminated together. As illustrated in FIG. 9, the separator 250 can comprise seven layers 252A-G of material. The layers 252 of the separator 250 can comprise, in order from the outermost layer to the innermost layer, a 12 um polyethylene terephthalate layer 252A, a first 3 um adhesive layer 252B, an 8 um aluminum layer 252C, a second 3 um adhesive layer 252D, a 15 um oriented polyamide layer 252E, a third 3 um adhesive layer 252F and a 75 um polypropylene layer 252G. All of the layers 252 are hermetically sealed to the lower portion of the valve housing 216.

The outer edges of the layers 252 can be sealed by a heat seal bonding process that uses heat and pressure to permanently bond the edges of the layers 252 to form a hermetically sealed edge 254. The separator 250 can be subsequently sealed to the valve housing 216 by a heat seal bonding process that uses heat and pressure to permanently bond the separator 250 to the valve housing 216.

Referring again to FIGS. 8 and 8A, the actuator top 262 has a cover housing 270 with an integrally formed actuator finger 272 and a thumb tab 274. The actuator finger 272 is separated along its sides by slots 276, has cam levers 278 that extend downward therefrom, and is resiliently cantilevered from a front portion of the cover housing 270. The actuator top 262 is formed from a resilient plastic material, preferably by injection molding. Alternatively, it is contemplated that the actuator finger 72 can be connected to the cover housing 70 by a hinge (not shown) instead of an integrally connection.

The handle base 264, best shown in FIG. 8, comprises an outer wall 280 having a slot 282 at one end in which is mounted the end of the dispensing tube 266. The handle base 264 further comprises a pair of arcuate inner walls 284, which with outer wall 280 forms cylindrical sockets for the aerosol chambers 10 and 14. The arcuate inner walls 284 each have a vertical slot extending from a top portion substantially identical with the slot 282 in the outer wall 280. A handle 288 is integrally formed with the outer wall 280 and is designed so that a user can grip the handle 288 with his or her hand and apply thumb pressure at thumb tab 274 to the actuator finger 272. An integral lock (not shown) can be formed on an outer end of the actuator finger 272 and project downwardly thereof to abut the handle 288 and prevent depression of the actuator finger 272 prior to sale and use of the dispenser. The integral lock can be attached to the handle 288 with a frangible connection and thus easily removed when it is desirable to dispense the contents of the aerosol chambers 10 and 14.

The dispensing tube 266, preferably formed from polypropylene, comprises connecting tubes 292 in fluid communication with the interior of a hollow conduit 290 having a closed end 294 and a nozzle end 296. The connecting tubes 292 have an open lower end sized to receive the hollow upper end of the valve stem 214. Dispensing tube 266 further comprises a hollow conduit insert 202. Hollow conduit insert 202 is a rod shaped structure that fits tightly against an upper wall of the hollow conduit 290 but leaves a cavity 203 of a predetermined volume at a lower wall of the hollow conduit 290. The cavity is in fluid communication with connecting tubes 292 and, therefore, with the hollow upper end of the valve stem 214. A mechanical breakup plug 204 can be located on one end of the conduit insert 202 and forms a part of the nozzle end 296. A spray aperture 206 of a predetermined size is formed at a lower portion of the mechanical breakup plug 204 and aligned with the cavity 103.

The aerosol dispenser 260 can be provided with various fixed spray nozzles, as shown in FIG. 2, depending on the desired spray pattern. Alternatively, the dispenser 260 can be provided with an adjustable spray nozzle 200, best seen in FIG. 8, for selectively delivering the contents of the dispenser 260 using a variety of spray patterns. Adjustable spray nozzles are well known and representative, non-limiting examples are shown in U.S. Pat. Nos. 4,174,069 and 4,227,650, which are incorporated herein by reference in their entirety. The dispensing tube 266 can comprise a threaded portion at an outlet end. The spray nozzle 200 is rotatably attached to the dispensing tube 266 at the threaded end and comprises an at least one generally circular terminal aperture 208, therethrough that is in fluid communication with the spray aperture 206 and, therefore, the cavity 203 and the connecting tubes 292. The mechanical breakup plug 204 and the adjustable spray nozzle 200 force a disrupted flow pattern at the nozzle end 296 of the hollow conduit 290 wherein the contents are mixed and delivered under pressure to the surface to be cleaned.

While the dispenser 260 has been illustrated with one type of handle and dispensing mechanism, it is within the scope of the invention for the dispenser 260 to have a handle and dispensing mechanism according to any of the embodiments of the invention.

The sealed and pressurized chambers 10, 14 are capable of containing excessive pressure created if the oxidant should come in contact with a reactant inside the chamber 10, 14, such as flaws in the separator 250, contact with an activator, or trace contaminants in the compounding solvents. The chamber 10, 14 is designed to an aerosol industry standard 18 bar strength level to provide an adequate safety margin. In the preferred embodiment, the container buckle strength is no less than 250 psi and the burst strength no less than 320 psi.

The chambers 10, 14 can also be provided with a pressure relief device such as any of those disclosed in U.S. Pat. Nos. 4,416,388, 4,433,791, 4,513,874 and 4,580,690, herein incorporated in full by reference.

In operation, the aerosol dispensers 60 and 260 function in a similar way. The aerosol chambers 10 and 14 are equipped with the push valve assemblies 110 in the dispenser 60 by attaching the cups 112 thereto and are releasably mounted within the outer walls 80 of the aerosol dispenser 60 so that the valve stems 114 are seated within the open outer end of the connecting tubes 92. The dispensing tube 66 fits within the slots 82 in the outer wall 80 and within the slots 86 in the arcuate inner walls 84 for vertical reciprocatory movement therein. The top surface of the dispensing tube 66 abuts the underside of the cam levers 78.

When a user grips the handle 88 and depresses the actuator finger 72 through thumb pressure at the thumb tab 74, the cam levers 78 are driven downwardly with respect to the handle base 64 to thereby depress the valve stems 114 and the springs 120 so that the valve orifices 126 in the stems 114 are positioned below the gasket 118. In this configuration, the valve orifices are in fluid communication with the housing 116 and the dip tube 122. As a result, the contents of the aerosol chamber are respectively dispensed in equal proportion through the push valve assembly 110 via the dip tube 122, the housing 116, the valve orifices, and the hollow upper end of the stem 114; through the connecting tubes 92; through the cavity 103 of the hollow conduit 90; through the spray aperture 106 of the mechanical breakup plug 104, and through the terminal aperture 108.

The pressure in the aerosol chambers 10 and 14 forces the contents of the chambers 10, 14 through the terminal aperture 108 in a spray pattern. When the pressure on the actuator finger 72 is released, the dispensing tube 66 rises in the slots 82 and 86 under spring pressure from the push valve assemblies 110 to cease the flow of liquid from the aerosol chambers 10, 14.

The aerosol dispenser 260 operates in much the same manner except that fluid flows from the separator 250 into the housing 216 through the fluid flow channel 222 in the housing 216 rather than through a dip tube 122, as in the aerosol dispenser 60. Depression of the actuator finger 272 by the user drives the cam levers 278 downward thereby depressing the valve stems 214 and the springs 220 so that the valve orifices 226 are in fluid communication with the housing 216 and the fluid flow channel 220. As a result, the contents of the separators 250 inside the aerosol chambers 10, 14 are respectively dispensed in equal proportion through the push valve assembly 200 via the housing 216, the valve orifices 226, and the hollow upper end of the stem 214; through the connecting tubes 292; through the cavity 203 of the hollow conduit 202; through the spray aperture 206 of the mechanical breakup plug 204, and through the terminal aperture 208.

The pressure in the aerosol chambers 10 and 14, between the sidewalls of the chambers 10, 14 and the separator bag 250 forces the contents of the separator bag 250 through the spray nozzle 208 in a desired spray pattern such as a mist, stream, cone-shaped, or flat spray. When the pressure on the actuator finger 272 is released, the dispensing tube 266 rises in the slots 282 and 286 under spring pressure from the push valve assemblies 210 to cease the flow of liquid from the aerosol chambers 10, 14.

The proper combination of valve orifice size 126, 226, cavity 103, 203, terminal aperture 108 or spray nozzle aperture 208 size, and propellant pressure are selected to achieve the desired ratio and flow rate of the contents of the separators 250 within the chambers 10, 14. The contents of each separator 250 can be mixed at an equal ratio. Alternatively, the size of the respective valve orifices 126, 226 on each separator 250 in each chamber 10, 14 can be varied to provide a desired mix ratio. For example, the valve orifice 126, 226 for the separator 250 in container 14 can be sized such that twice as much liquid is released into the cavity 103, 203 from the separator 250 in container 14 compared to the separator 250 in container 10 upon actuation of the cam lever 178, 278.

The aerosol dispensers 60 and 260 disclosed above can be used to dispense a variety of compositions having one or more components that are preferably not mixed until just prior to or during dispensing of the composition. Isolating one or more components from the remainder of the composition can increase the stability, shelf life and efficacy of the composition.

While the dispenser 60 is illustrated having two chambers 10, 14 that do not contain a separator pouch 250, it is within the scope of the invention for one of the containers 10, 14 of the dispenser 60 to contain a separator pouch 250 while the other does not. Similarly, while the dispenser 260 is illustrated having two chambers 10, 14 both containing a separator pouch 250, it is within the scope of the invention for one of the containers 10, 14 of the dispenser 260 to contain a separator pouch 250 while the other does not.

The following are non-limiting examples of areas of use for the container dispensers 60 and 260 disclosed herein.

Cleaning Compositions

In the case of a cleaning composition having hydrogen peroxide, the hydrogen peroxide can degrade over time or react with one or more components present in the cleaning composition, resulting in a composition that has a decreased concentration of hydrogen peroxide over time. This can result in decreased cleaning efficiency over time. Storing the hydrogen peroxide in a container separate from the remainder of the cleaning composition increases the stability and shelf life of the hydrogen peroxide, resulting in a cleaning composition that maintains its cleaning efficiency over a longer period of time.

A fabric/carpet cleaning formula composition for removing stains and soil from carpets and fabrics such as upholstery fabrics is filled into one of the aerosol chambers 10, 14 according to the embodiment illustrated by dispenser 60. Alternatively, the cleaning composition can be filled into a pouch 250 within one of the chambers 10, 14 according to the embodiment illustrated by dispenser 260. This composition includes one or more cleaning solvents, a surfactant, de-ionized water and, optionally, a fragrance. According to the invention, the cleaning composition further includes a pH adjusting agent to maintain a pH in the cleaning solution between 7.5 and 12.0 in order to trigger release of oxygen in the oxidizing composition. The cleaning composition can also include an anti-stain and/or anti-resoil agent. An example of the anti-stain protectant is PM 1874, a sulfo-methacrylate resin, manufactured by the 3M Company. An example of the anti-soil component is PM 1870, a polysilosane derivative in the silsesquioxane chemical family, also manufactured by the 3M Company. Other components may include acrylic polymers.

De-ionized water is preferred as the solvent medium for the cleaning composition. The de-ionized water minimizes contamination of the cleaning solution from trace minerals in the water. One advantage of using de-ionized water as a solvent is that it evaporates with little or no residue after delivering cleaning agents to the carpet or upholstery. Alternative cleaning solvents can be one or more glycol ethers, for example dipropylene glycol monomethyl ether, or Glycol Ether DPM, and propylene glycol normal propyl ether, Glycol Ether PNP, or one of the terpenes such as natural terpenes including d-limonene. These components can be present in the cleaning composition in effective amounts. For example, the Glycol Ether DPM can be present in the range of 0.5 to 1.5, preferably 0.8 wt. % in the composition. Glycol Ether PNP can be present in the range of 0.8-15.0, preferably 7.2 wt. %. D-limonene, when used, can be present in the range of 0.1 to 5.0, preferably 0.3 wt. % in the composition.

Non-ionic surfactants can be present in a range of about 0.1 to 2.0. Tomadol 23-6.5, a non-ionic surfactant comprising ethylene oxide attached to lineal alcohol, is preferably present at about 0.8 wt. %. Alternatively, Neodol 23-6.5, another alcohol ether, can be present at about 1.8 wt. %.

The EDTA can be present in amounts between about 0.1 and 5.0, preferably 0.4 wt %, in compositions that include 40% EDTA solution.

According to the embodiment illustrated by dispenser 60, the propellant is preferably dimethyl ether ($C_2H_6O$, also known as DME). An alternative propellant can be the hydrofluorocarbon (HFC) family, particularly 1,1-difluoroethane ($CH_3CHF_2$). A suitable commercially available HFC is Dymel 152A from Dupont. The concentration of Dymel 152A in the cleaning composition can be in the range of 1%-25% by weight and preferably 5%. Yet other alternative propellants include hydrocarbons such as isobutane ($C_4H_{10}$), propane ($C_3H_8$), and liquefied petroleum gas; and natural gases including compressed air, carbon dioxide, and nitrogen.

Pressurization within the cleaning composition chamber 10, 14 according to the embodiment illustrated by dispenser 60 can range from 1 to 100 pounds per square inch (psi). When DME is the propellant, dual 0.020 inch push valve orifices and an internal pressure of 45 psi are preferred. When a HFC propellant is used, a single 0.020 inch orifice is employed at an internal pressure of 70 psi.

According to the embodiment illustrated by the dispenser 260, a suitable propellant for filling the space between the separator 250 and an interior surface of the chambers 10, 14 includes nitrogen or compressed air. Pressurization within the chambers 10, 14 of the dispenser 260 can range from 50-150 psig with a preferred range from 110-120 psig.

The pH adjusting agent is also used to remove trace amounts of iron and other contaminates. A typical pH agent is EDTA (ethylenedietetramine). Other suitable pH agents include disodium EDTA, an example of which is Hampene Na2.

The cleaning composition can further include an activator for the oxidizing composition. The preferred activator is sodium carbonate, however, other suitable activators include metals ions, metals salts, and other carbonates such as sodium bicarbonate. Still other suitable activators include tetraacetylethylenediamine, sodium octanoyloxybenzene sulfonate, sodium nonanoyloxybenzene sulfonate, sodium decanoyloxybenzene sulfonate, (6-octanamido-caproyl) oxybenzenesulfonate, (6-nonanamido-caproyl) oxybenzenesulfonate, 6-decanamido-caproyl) oxybenzenesulfonate, and mixtures thereof. In the preferred embodiment, sodium carbonate can be added as an activator in an amount of at least 0.1 wt. % and preferably 0.5 wt. % to reach a stoichiometric ratio of activator to reactant.

The cleaning composition can also include anionic surfactants that create a friable residue that can be vacuumed after the cleaning process. A suitable anionic surfactant is sodium lauroyl sarcosinate, such as Hamposyl L-30 Type 724, and can be present in suitable amounts, for example between 1.0 and 6.0, preferably 3.3 wt. %.

In addition to the foregoing, the cleaning composition can further include a dispersant for soil and a further pH stabilizer such as Alcosperse 602N, which is an acrylate polymer.

The oxidizing composition is filled into the other aerosol chamber 10, 14 according to the embodiment illustrated by dispenser 60 and includes de-ionized water, a peroxygen compound, a stabilizer and, optionally, anti-soil and/or anti-stain protectants. Alternatively, the oxidizing composition can be filled into a pouch 250 within the chamber 10, 14 according to the embodiment illustrated by dispenser 260. An example of the anti-stain protectant is PM 1874, manufactured by the 3M Company. An example of the anti-soil component is PM 1870 from the silsesquioxane chemical family, also manufactured by the 3M Company. Other components may include acrylic polymers. Suitable soil-resist or anti-soil compositions are disclosed in the U.S. Pat. No. 5,888,290, which is incorporated herein by reference.

The de-ionized water in the oxidizing solution is present in a range of about 70 to about 99 wt. %, preferably about 88.3 wt. %. De-ionized water is important in the oxidizing solution to minimize contaminants that will initiate activation inside the chamber, reducing the cleaning efficacy of the composition and creating an undesirable increase in internal pressure. The peroxygen compound can be present in a range of about 0.4% to 29%, preferably 11.4%, of the active ingredients resulting in a total fill concentration of about 0.1%-10% by weight with a preferred value of about 4 wt. %.

The peroxygen compound is preferably a cosmetic grade hydrogen peroxide ($H_2O_2$), however other peroxygen compounds can be used. A suitable commercially available 35% cosmetic grade hydrogen peroxide is available from the Degussa Company and is preferred because of its superior stability characteristics and extended shelf life. Other suitable hydrogen peroxides are available from Solvay Interox. Yet another suitable hydrogen peroxide is provided by FMC Industrial Chemicals under the trade names Hybrite 32.5%, Durox, Oxypure 35%, Standard 27.5 35%, Super D 25 and 35, Technical 35%, Chlorate Grade 20%, Semiconductor Reg, Seg, RGS, RGS 2, RGS 2, 31%. Alternatively, the peroxygen compound can be a preformed peracid compound selected from the group consisting of percarboxylic acid and salts, percarbonic acids and salts, perimidic acids and salts, peroxymonosulfuric acids and salts, and mixtures thereof, a persalt such as perborate compounds, percarbonate compounds, perphosphate compounds and mixtures thereof, or a peroxide compound.

The anti-stain ingredient in the oxidizing solution can be present in about 1 to 5 wt. %, typically about 1.7 wt. %. The anti-soil ingredient is typically present in less than 1% by weight, typically about 0.3 wt. % in the composition.

The pH stabilizer will maintain the oxidizing composition at a pH level in the range of 1.5 to 8.5, preferably about 6.8. Pentasodium diethylenetriamine pentaacetate, for example Versenex 80, is an appropriate pH stabilizer when oxidative conditions exist. It will also neutralize any trace elements of contaminates in the oxidizing composition.

According to the embodiment illustrated by dispenser 60, the aerosol propellant for the oxidizing composition is preferably dimethyl ether ($C_2H_6O$, also known as DME). Alternative propellants may be chosen from the hydrofluorocarbon (HFC) family, hydrocarbons, and natural gasses. A suitable HFC is 1,1-difluoroethane ($CH_3CHF_2$), commercially available as Dymel 152A from Dupont. The concentration of Dymel 152A in the oxidizing composition can be in the range of 1%-25% by weight, preferably 5%. A particularly suitable hydrocarbon is N-Butane ($C_4H_{10}$). Alternative hydrocarbon materials include isobutane ($C_4H_{10}$), propane ($C_3H_8$), and liquefied petroleum gas. Natural gases include compressed air, carbon dioxide, and nitrogen.

Pressurization within the oxidizing chamber can range from 1 to 100 pounds per square inch (psi). When DME is the propellant, a single 0.020 inch orifice is preferred at a preferred pressure of about 45 psi. Alternatively, dual 0.020 inch orifices can be employed with DME. When HFC is the propellant, a single valve orifice of 0.018 inches is used and the preferred pressure is about 70 psi.

According to the embodiment illustrated by the dispenser 260, a suitable propellant for filling the space between the separator 250 and an interior surface of the chambers 10, 14 includes nitrogen or compressed air. Pressurization within the chambers 10, 14 of the dispenser 260 can range from 50-150 psig with a preferred range from 110-120 psig.

The pH values of the cleaning composition and the oxidizing composition can vary over a wide range but are selected, taking into consideration the volume of each composition that is dispensed simultaneously, so that the pH of the combined cleaning composition and the oxidizing composition is sufficiently greater than 7 to activate the discharge of oxygen from the oxidizing solution for enhanced cleaning of the carpet surface. In a preferred embodiment the pH is the combined cleaning composition and the cleaning composition is greater than 8, preferably about 8.3.

EXAMPLES

Spot cleaning compositions were prepared with the following ingredients in Table 1:

TABLE 1

| CLEANING COMPOSITIONS | | | | | | | | |
|---|---|---|---|---|---|---|---|---|
| INGREDIENTS | A | E | B | F | G | C | D | H |
| Deionized Water | 83.40 | 83.67 | 82.90 | 83.40 | 83.50 | 83.80 | 90.80 | 89.35 |
| Sodium Carbonate | 0.50 | 0.40 | 0.50 | 0.50 | 0.50 | | | |
| Dowanol PNP[1] | 15.00 | 15.00 | 14.70 | 15.00 | 14.80 | 15.00 | | |
| Fragrance[2] | 0.10 | 0.10 | | | | 0.10 | 0.10 | 0.05 |
| Tomadol 23-6.5[3] | 0.80 | 0.66 | 0.80 | 0.66 | 0.80 | 0.60 | 0.70 | |
| Petro ULF[4] | 0.20 | 0.17 | 0.80 | 0.34 | 0.20 | | | |
| d-limonene | | | 0.30 | 0.10 | 0.30 | | | |
| EDTA, 40% | | | | | | | 0.40 | 0.40 |
| Glycol Ether DPM | | | | | | | 0.80 | 0.50 |
| Glycol Ether PNP | | | | | | | 7.20 | 4.50 |
| Hampene Na2[5] | | | | | | | 0.50 | |
| Neodol 23-6.5[6] | | | | | | | 1.80 | |
| Hamposyl L-30 Type 724[7] | | | | | | | 3.30 | |
| Alcosperse 602N[8] | | | | | | | | |

| INGREDIENTS | I | L | J | K | M | O | N | P |
|---|---|---|---|---|---|---|---|---|
| Deionized Water | 88.85 | 85.80 | 82.90 | 82.90 | 87.00 | 89.70 | 89.9 | 90.80 |
| Sodium Carbonate | | | | | | | | |
| Dowanol PNP[1] | | | | | | | | |
| Fragrance[2] | 0.05 | 0.10 | 0.10 | 0.10 | 0.10 | 0.10 | 0.10 | 0.10 |
| Tomadol 23-6.5[3] | | | | | | | | |
| Petro ULF[4] | | | | | | | | |
| d-limonene | | | | | | | | |
| EDTA, 40% | | | | | | | 0.50 | 0.40 |
| Glycol Ether DPM | 0.50 | 0.80 | 1.50 | | 7.20 | 0.80 | 7.20 | 0.80 |
| Glycol Ether PNP | 4.50 | 7.20 | 13.50 | 15.00 | 0.80 | 7.20 | 0.80 | 7.20 |
| Hampene Na2[5] | | | | | | | | |
| Neodol 23-6.5[6] | 1.80 | 1.80 | 1.00 | 1.00 | 0.40 | 0.70 | 0.50 | 0.70 |
| Hamposyl L-30 Type 724[7] | 3.30 | 3.30 | | | 3.00 | | 1.00 | |
| Alcosperse 602N[8] | 1.00 | 1.00 | 1.00 | 1.00 | 1.50 | 1.50 | | |

[1]Glycol ether, a solvent, manufactured by Dow Chemical Company
[2]Sapphire fragrance, manufactured by Firmenich
[3]Linear primary alcohol ethoxylate, a non-ionic surfactant, manufactured by Tomah Chemical Company
[4]Sodium alkyl napthelene sulfonate from AKZO Nobel
[5]Disodium EDTA, manufactured by Hampshire Chemical
[6]Alcohol ether, a non-ionic surfactant, manufactured by Shell Chemicals
[7]Sodium lauroyl sarcosinate, an anionic surfactant, manufactured by Hampshire Chemical
[8]Acrylate polymer, a pH stabilizer, manufactured by Alco Chemical For all of the samples, the pH of the cleaning composition was 11.3±0.3. The compositions of the oxidizing solutions were as follows in Table 2:

TABLE 2

| OXIDIZING SOLUTIONS | | | |
|---|---|---|---|
| INGREDIENTS | A | B | C |
| Deionized Water | 88.30 | 77.70 | 79.70 |
| Hydrogen Peroxide, Cosmetic Grade 35% | 11.40 | 20.00 | 20.00 |
| Versenex 80[1] | 0.30 | 0.30 | 0.30 |
| PM 1874[2] | | 1.70 | |
| PM 1870[3] | | 0.30 | |

[1]Pentasodium diethylenetriamine pentaacetate, a pH stabilizer, manufactured by Dow Chemical Company
[2]Sulfo-methacrylic polymer, an anti-stain protectants, manufactured by the 3M Company
[3]Polysilosane derivative, an anti-soil ingredient, manufactured by the 3M Company For all of the samples, the pH of the oxidizing solution was 6.8±0.3.

Any of the cleaning compositions may be combined with any of the oxidizing solutions to achieve acceptable cleaning results. The preferred combinations are shown in Table 3. Although any combination of cleaner and oxidizer will result in acceptable results, each combination exhibits different characteristics. From a chemistry perspective, the technically superior result is a combination of cleaner A and oxidizer A. However, when cost of ingredients is taken into account, cleaner C combined with oxidizer A is the best choice for consumer value. The best cleaning performance was exhibited by cleaner A combined with oxidizer C, and the best protection was provided by cleaner A combined with oxidizer B.

TABLE 3

PREFERRED COMBINATIONS

| COMPOSITION | TECHNICALLY SUPERIOR | SUPERIOR CLEANER | SUPERIOR PROTECTION | MARKET CHOICE |
|---|---|---|---|---|
| Cleaning Composition | A | A | A | C |
| Oxidizing Solution | A | C | B | A |

The pH of the combined cleaning composition and oxidizing solution as expelled for all samples was 8.3±0.3.

Test Method

Two separate chambers were partially filled with the carpet cleaning solution and the oxidizing solution. The chambers were then partially filled with an aerosol propellant. The two compositions were then dispensed through a common spray nozzle onto carpet samples that had been pretreated with stains from red wine, grape juice, spaghetti sauce, chocolate syrup, red lipstick, and blue ballpoint pen ink. The carpets were scrubbed moderately with a brush and then were vacuumed with a suction cleaner to remove the soiled solution. Cleaning was measured using a calibrated spectrophotometer on the stain at both the front and back of the carpet sample. Results were calculated as $\Delta E$, the difference in spectrophotometer readings from the clean, virgin carpet and the carpet after the stain was removed ($\Delta E$=virgin reading−cleaned reading). The lower the $\Delta E$ value, the less stain remains. The stains were satisfactorily removed. The average results for each stain for the preferred combination of cleaner C and oxidizer A (Market Choice from Table 3) are presented in Table 4.

TABLE 4

RESULTS OF SIGNIFICANT OUTCOMES FOR MARKET CHOICE

| STAIN | $\Delta E$ VALUE |
|---|---|
| Grape Juice | 2.97 |
| Koolaid (Cherry) | 8.03 |
| Coffee | 5.99 |
| Red Wine | 3.72 |
| Cola | 1.59 |
| Lipstick (Red) | 15.97 |
| Spaghetti | 13.67 |
| Black Ink | 44.25 |
| Dirty Motor Oil | 21.26 |
| Chocolate Syrup | 27.27 |

Neutralizer for Chemical or Biological Species

According to another embodiment of the invention, the dispensers 60 and 260 can be used to dispense a chemical or biological agent neutralizer or decontaminator, such as those disclosed in U.S. Pat. No. 6,566,574 to Tadros et al., U.S. Pat. No. 7,390,432 to Tucker, and U.S. Pat. Nos. 7,271,137, 6,723,890 and 7,125,497 to Tucker et al. described above. A reactive component, such as an oxidizing agent or nucleophilic or combinations thereof, can be stored in a first chamber 10, 14 and the other components, such as solubilizing agents, peroxide activators and bleaching activators can be stored in the second chamber 10, 14. The reactive components must be stored separately from components such as peroxide and bleaching activators as these components can react during storage resulting in a neutralizer with decreasing efficacy over time.

The solubilizing agents can be a mixture of one or more cationic surfactants, cationic hydrotropes and fatty alcohols. Examples of suitable cationic surfactants include: quaternary ammonium salts and polymeric quaternary salts. Examples of suitable quaternary ammonium salts include: cetyltrimethyl ammonium bromide, benzalkonium chloride, benzethonium chloride, cetylpyridinium chloride, alkyldimethylbenzylammonium salt, and tetrabutyl ammonium bromide. A preferred cationic surfactant is WITCO VARIQUAT 80MC.™ which is a mixture of benzyl (C12-C16) alkyldimethylammonium chlorides.

Examples of suitable cationic hydrotropes include: tetrapentyl ammonium bromide, triacetyl methyl ammonium bromide, and tetrabutyl ammonium bromide. A preferred cationic hydrotrope is WITCO ADOGEN 477.™ which is a pentamethyltallow alkyltrimethylenediammonium dichloride.

The fatty alcohol can be a alcohol having 8-20 carbon atoms per molecule. Examples of suitable fatty alcohols include 1-dodecanol, 1-tridecanol, hexadecanol and 1-tetradecanol or a mixture thereof.

The reactive component can be a mixture of one or more oxidizing and/or nucleophilic reagents. Examples of suitable reactive compounds include: peroxide compounds; hydrogen peroxide; urea hydrogen peroxide; sodium perborate; sodium percarbonate; sodium carbonate perhydrate; sodium peroxypyrophosphate; sodium peroxysilicatehydrogen; peroxide adducts of pyrophosphates; citrates; sodium sulfate; urea; and sodium silicate; an activated peroxide compound (e.g., hydrogen peroxide+bicarbonate); peracetic acid; oximates (e.g., butane-2,3-dione, monooximate ion, and benzohydroxamate); alkoxides (e.g., methoxide and ethoxide); aryloxides (e.g., aryl substituted benzenesulfonates); aldehydes (e.g., glutaraldehyde); peroxymonosulfate; Fenton's reagent (a mixture of iron and peroxide); and sodium hypochlorite.

Use of these reactive compounds in DF-200 formulations can produce a variety of negatively-charged nucleophiles, e.g., hydroxyl ions ($OH^-$) and hydroperoxide ions ($OOH^-$) produced when using hydrogen peroxide; and/or hydroperoxycarbonate ions ($HCO_4^-$) produced when hydrogen peroxide is combined with a carbonate salt. Hydroperoxycarbonate ions ($HCO_4^-$) are a much stronger oxidant than hydroxyl ions ($OH^-$) or hydroperoxide ions ($OOH^-$), and are especially effective in reacting with biological toxants.

The reactive component can also comprise a reducing compound or an acid. The reducing compound can be selected from the group consisting of sodium bisulfite, ferrous sulfide, sodium sulfide, sodium thioglycollate, sodium thiosulfate, sodium borohydride and combinations thereof. The acid can be selected from the group consisting of sodium bisulfate, citric acid, acetic acid, nitrous acid, hydrocyanic acid, hydrogen sulfide, phenols and combinations thereof.

Bleaching activators can be compounds with O- or N-bounded acetyl groups that react with the strongly nucleophilic hydroperoxy anion ($OOH^-$) to yield peroxygenated species, which are more efficient oxidizers than hydrogen peroxide alone. Examples of suitable bleaching activators include: ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, propylene glycol diacetate, tetraacetyl ethylenediamine (TAED), and n-nonanoyloxybenzenesulfonate (NOBS).

The neutralizing composition can also contain peroxide activators in the form of carbonate salts that can combine with a reactive compound, e.g. hydrogen peroxide, to form the highly reactive hydroperoxycarbonate species ($HCO_4^-$). The addition of carbonate salts can also buffer the formulation to optimize the pH. Examples of suitable peroxide activators include: potassium bicarbonate, sodium bicarbonate, ammonium bicarbonate, ammonium hydrogen bicarbonate, lithium bicarbonate, ammonium carbonate, and potassium carbonate.

The dispensers 60 and 260 provide a way to store the neutralizing composition as a two part kit that is immediately available for use as needed. For example, a reactive component, such as hydrogen peroxide can be stored in a first container 10 and the solubilizing agent, such as a cationic surfactant and a bleaching activator, such as glycerol diacetate, for example, can be stored in a second container 14. Each container can also contain various other ingredients such as solvent and buffers for example, depending on their compatibility. The components of each chamber 10, 14 can be mixed at the right ratios and dispensed from the dispensers 60 and 260 as described above as needed.

The two container dispensers 60 and 260 described herein provide a device for stably storing the components of a chemical or biological agent neutralizer that is immediately available for use without requiring the user to prepare, mix or dilute a solution. This can save valuable time in the instance of contamination with a chemical or biological species.

Exothermic Reactions

According to another embodiment of the invention, the dispensers 60 and 260 can be used to dispense a heat-producing composition, wherein the heat is provided by the reaction of one or more components stored separately in each aerosol chamber 10, 14. The components can react as they are being dispensed to produce a heated solution. A heated solution can provide improved cleaning capabilities for a cleaning composition or increase the efficiency of a disinfecting or sterilizing solution. Examples of compositions and systems for generating heat in the cleaning and/or oxidizing solutions are disclosed in U.S. Pat. No. 7,153,371, which issued on Dec. 26, 2006, and is incorporated herein by reference.

Active Film Formers

According to another embodiment of the invention, the dispensers 60 and 260 can be used to dispense components that are liquid in their individual states but react to form matter having a different state. For example, the chambers 10, 14 can be used to store two-part epoxy glues. In another example, a glue, such as cyanoacrylate, or a paint can be stored in a first chamber 10, 14 and an appropriate hardener can be stored in a second chamber 10, 14. In yet another example, a repellant car wax or polish or a windshield water repellant can be stored in a first chamber 10, 14 and an appropriate catalyst can be stored in a second chamber 10, 14.

Color Change Chemistry

According to another embodiment of the invention, the dispensers 60 and 260 can be used to dispense components that can react to produce a color or a color change. The color could be used to indicate coverage of the dispensed liquid or the color could be used as a built in time for indicating that the dispense liquid had dried, for example.

Health & Beauty Aids/Medical

According to another embodiment of the invention, the dispensers 60 and 260 can be used to dispense components that react to produce an active composition. For example, a hair dye or bleach can be stored in a first container and an appropriate activator can be stored in the second container. Additional examples include skin lighteners and bleaches, self tanners, teeth whiteners, oral rinses, spray bandages and spray casts for broken bones.

Emulsions

According to another embodiment of the invention, the dispensers 60 and 260 can be used to dispense components that interact upon mixing to produce an emulsion. An oil can be stored in a first chamber 10, 14 and an emulsifier and water can be stored in a second chamber 10, 14. Examples include producing an instant mayonnaise or salad dressing product.

Paints

According to another embodiment of the invention, the dispensers 60 and 260 can be used to dispense paint and an enhancer or modifier. Paint can be stored in a first chamber 10, 14 and an enhancer or modifier can be stored in a second chamber 10, 14. Examples of an enhancer or modifier include hardeners, antimicrobial agent, deodorant, clear coat, glitters, metallic particles, texturizers, crackle coating, marbleizing coating, antiquing or oxidizing coating for producing a patina effect and viscosity builders. Alternatively, the second container can container a second paint having a different color for producing a camouflage effect, for example. In another example, the first container can contain a resin and solvent and the second container can contain the colorant for generating the paint as it is dispensed.

Automotive

According to another embodiment of the invention, the dispensers 60 and 260 can be used to dispense one or more compounds that can react to generate a gas to inflate a tire. For examples, a first chamber 10, 14 can contain a sodium carbonate solution and the second chamber 10, 14 can contain a citric acid solution. The sodium carbonate and citric acid can react during dispensing to generate carbon dioxide, which can be used to inflate an automotive or bicycle tire. This chemistry has an advantage over existing technology in which a flammable propellant is used Home Construction & Maintenance According to another embodiment of the invention, the dispensers 60 and 260 can be used to dispense a material and an additive. For example, a bathtub glazing system can comprise a sealant stored in a first chamber 10, 14 and a protectant stored in a second chamber 10, 14. In another example, a wood stain can be stored in a first chamber 10, 14 and a varnish can be stored in a second container.

According to yet another example, a foam sealant chemistry can be dispensed, wherein a first chamber 10, 14 contains a sodium bicarbonate solution and a second chamber 10, 14 contains a citric acid solution. The bicarbonate and citric acid solutions react during dispensing to generate a gas, carbon dioxide, that can foam the sealant chemistry, causing it to expand and fill in voids. The foam sealant chemistry can also be used in packaging items in a container. The foam can expand to fill in voids around items packaged in a container to protect the items during transport and storage.

Reasonable variation and modification are possible within the forgoing disclosure and drawings without departing from the spirit of the invention that is defined in the appended claims.

We claim:

1. A kit for dispensing a mixture of two compositions comprising:
   a container comprising:
      a first chamber and a second chamber, wherein at least one of the first and second chambers has a separator in the form of a pouch for physically separating the contents of the chamber from an interior surface of the chamber; and
      a dispensing system connected to the first and second chambers and having a single dispensing spray outlet for simultaneously dispensing and mixing controlled amounts of liquid from each of the first and second chambers;
   a first composition comprising a solubilizing composition;
   a second composition different from the first composition and having a reactive component that reacts with at least one compound upon mixing;
   an aerosol propellant between the separator and the interior surface of the at least one of the first and second chambers for pressurizing the contents in the pouch for dispensing the contents thereof through the dispensing system under pressure; and
   wherein when the first composition is stored in the first chamber and the second composition is stored in the second chamber, the dispensing system can simultaneously dispense a mixture of the first and second compositions from the container under pressure.

2. The kit for dispensing a mixture of two compositions according to claim 1 wherein the first composition is a cleaning composition and the second composition is an oxidizing composition.

3. The kit for dispensing a mixture of two compositions according to claim 2 wherein the cleaning composition comprises at least one of a solvent, a surfactant, an anti-stain compound, an anti-soil compound, a fragrance and mixtures thereof.

4. The kit for dispensing a mixture of two compositions according to claim 2 wherein the oxidizing composition comprises at least one of an oxidizing agent, an anti-stain compound, an anti-soil compound, a stabilizer and mixtures thereof.

5. The kit for dispensing a mixture of two compositions according to claim 4 wherein the oxidizing agent is selected from the group consisting of hydrogen peroxide, percarboxylic acids and salts, percarbonic acids and salts, perimidic acids and salts, peroxymonosulfuric acids and salts, and mixtures thereof.

6. The kit for dispensing a mixture of two compositions according to claim 1 wherein the solubilizing composition comprises at least one of a cationic surfactant, a cationic hydrotrope, a fatty alcohol and mixtures thereof.

7. The kit for dispensing a mixture of two compositions according to claim 6 wherein the cationic surfactant comprises at least one of a quaternary ammonium salt, a polymeric quaternary salt and mixtures thereof.

8. The kit for dispensing a mixture of two compositions according to claim 6 wherein the cationic hydrotrope comprises at least one of tetrapentyl ammonium bromide, triacetyl methyl ammonium bromide, tetrabutyl ammonium bromide and mixtures thereof.

9. The kit for dispensing a mixture of two compositions according to claim 6 wherein the fatty alcohol is an alcohol having 8-20 carbon atoms.

10. The kit for dispensing a mixture of two compositions according to claim 1 wherein the solubilizing composition comprises at least one bleaching activator selected from the group consisting of ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, propylene glycol diacetate, tetraacetyl ethylenediamine (TAED), and n-nonanoyloxybenzenesulfonate (NOBS).

11. The kit for dispensing a mixture of two compositions according to claim 1 wherein the solubilizing composition comprises at least one peroxide activator selected from the group consisting of potassium bicarbonate, sodium bicarbonate, ammonium bicarbonate, ammonium hydrogen bicarbonate, lithium bicarbonate, ammonium carbonate, and potassium carbonate.

12. The kit for dispensing a mixture of two compositions according to claim 1 wherein the reactive component comprises at least one of an oxidizing agent, a reducing agent, a nucleophilic agent, an acid and mixtures thereof.

13. The kit for dispensing a mixture of two compositions according to claim 12 wherein the at least one oxidizing agent is selected from the group consisting of hydrogen peroxide, urea hydrogen peroxide, hydroperoxycarboflate, peracetic acid, sodium perborate, sodium peroxypyrophosphate, sodium peroxysilicate, sodium percarbonate, hydroperoxycarbonate, peroxymonosulfate, Fenton's reagent and sodium hypochlorite.

14. The kit for dispensing a mixture of two compositions according to claim 12 wherein the at least one nucleophilic agent is selected from the group consisting of oximates, alkoxides, aryloxides and aldehydes.

15. The kit for dispensing a mixture of two compositions according to claim 12 wherein the at least one reducing agent is selected from the group consisting of sodium bisulfite, ferrous sulfide, sodium sulfide, sodium thioglycollate, sodium thiosulfate and sodium borohydride.

16. The kit for dispensing a mixture of two compositions according to claim 12 wherein the at least one acid is selected from the group consisting of sodium bisulfate, citric acid, acetic acid, nitrous acid, hydrocyanic acid, hydrogen sulfide and phenols.

17. A method for neutralizing at least one of a chemical and biological species comprises:
   filling a first pouch in a first chamber with a solubilizing composition comprising at least one solubilizing agent for solubilizing the at least one of a chemical and biological species;
   filling a second pouch in a second chamber with a reactive composition comprising at least one reactive component that acts on the at least one of a chemical and biological species solubilized by the at least one solubilizing agent;
   simultaneously spraying the solubilizing composition and the reactive composition under pressure from their respective first and second pouches onto the at least one of a chemical and biological species; and
   injecting an aerosol propellant in a space between the first pouch and the first chamber and the second pouch and the second chamber to pressurize the first and second pouches, respectively, prior to the spraying act.

18. The method of claim 17 wherein the solubilizing and reactive compositions are mixed together as they are sprayed onto the at least one of a chemical and biological species.

19. The method of claim 17 wherein the solubilizing and reactive compositions are mixed together just prior to being sprayed onto the at least one of a chemical and biological species.

20. The method of claim 17 further wherein the solubilizing and reactive compositions are sprayed from their respective first and second chambers in equal amounts.

21. The method of claim 17 further wherein the solubilizing and reactive compositions are sprayed from their respective first and second chambers in unequal amounts.

22. The method of claim 17 wherein the solubilizing and reactive compositions are selectively sprayed as at least one of a mist, a spray, a stream and combinations thereof.

23. The method according to claim 17 wherein the solubilizing composition comprises at least one of a cationic surfactant, a cationic hydrotrope, a fatty alcohol and mixtures thereof.

24. The method of claim 23 wherein the solubilizing composition further comprises at least one bleaching activator selected from the group consisting of ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, propylene glycol diacetate, tetraacetyl ethylenediamine (TAED), and n-nonanoyloxybenzenesulfonate (NOBS).

25. The method of claim 23 wherein the solubilizing composition further comprises at least one peroxide activator selected from the group consisting of potassium bicarbonate, sodium bicarbonate, ammonium bicarbonate, ammonium hydrogen bicarbonate, lithium bicarbonate, ammonium carbonate, and potassium carbonate.

26. The method according to claim 23 wherein the reactive component comprises at least one of an oxidizing agent, a reducing agent, a nucleophilic agent, an acid and mixtures thereof.

* * * * *